(12) United States Patent
Mizutani et al.

(10) Patent No.: US 8,703,182 B2
(45) Date of Patent: Apr. 22, 2014

(54) LIGHT-STABILIZED SOFT CAPSULE FORMULATIONS

(75) Inventors: Akihiko Mizutani, Toshima-ku (JP);
Hisakazu Katsuki, Kita-ku (JP);
Kenichi Sakai, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1106 days.

(21) Appl. No.: 12/572,971

(22) Filed: Oct. 2, 2009

(65) Prior Publication Data

US 2010/0021535 A1    Jan. 28, 2010

Related U.S. Application Data (62) Division of application No. 10/510,644, filed as application No. PCT/JP03/05823 on May 9, 2003, now abandoned.

(30) Foreign Application Priority Data

May 9, 2002 (JP) ................................. 2002-134070

(51) Int. Cl.
*A61K 9/48* (2006.01)
(52) U.S. Cl.
USPC ......................................... 424/451; 514/774
(58) Field of Classification Search
CPC ..................................................... A61K 9/48
See application file for complete search history.

(56) References Cited

U.S. PATENT DOCUMENTS

| 3,784,684 A | 1/1974 | Bossert et al. |
|---|---|---|
| 6,893,658 B1 | 5/2005 | Iida et al. |
| 2003/0096115 A1 * | 5/2003 | Kozaki et al. ................. 428/404 |

FOREIGN PATENT DOCUMENTS

| EP | 0228067 A2 | 7/1987 |
|---|---|---|
| EP | 1208843 A1 | 5/2002 |
| JP | 57-4345 A | 1/1982 |
| JP | 58109415 A | 6/1983 |
| JP | 58-121211 A | 7/1983 |
| JP | 59-139317 A | 8/1984 |
| JP | 59-88420 | 5/1987 |
| JP | 63-166824 A | 7/1988 |
| JP | 5004925 A | 1/1993 |
| WO | 01/015702 | 3/2001 |

OTHER PUBLICATIONS

International Search Report by the European Patent Office in application No. EP 03725766 mailed on Apr. 5, 2011.

* cited by examiner

*Primary Examiner* — Hasan Ahmed
(74) *Attorney, Agent, or Firm* — Browdy and Neimark, PLLC (57) ABSTRACT

An object of the present invention is to provide a small-sized light-stabilized soft capsule formulation, which has a shell that ensures effective light shielding of an active ingredient encapsulated thereby.

The present invention provides a light-stabilized soft capsule formulation comprising a shell containing a non-water-soluble light-shielding agent and having an average thickness of 200 μm or less, and a medicament encapsulated by the shell.

3 Claims, 5 Drawing Sheets

LIGHT-STABILIZED SOFT CAPSULE FORMULATIONS

TECHNICAL FIELD

The present invention relates to light-stabilized soft capsule formulations having a shell that ensures effective light shielding of a medicament encapsulated thereby, as well as to a method for manufacturing the same. More particularly, the present invention relates to thin-shelled light-stabilized soft capsule formulations having a thin shell that ensures effective light shielding of a medicament encapsulated thereby.

BACKGROUND ART

Dosage forms conventionally used for the formulation of light-unstable substances include coated tablets, hard capsules, soft capsules, as well as oral solutions and powders filled in light-shielding containers. For example, JP 5-15691 B reports an example of soft capsule formulation whose shell is supplemented with 0.2 wt % of titanium oxide. Also, JP 57-4345 B reports an example of hard capsule formulation which contains 2 wt % or less of titanium oxide in combination with 0.5 wt % or less of iron oxide red. In certain cases such as where light-unstable substances are in a liquid form (e.g., oils, suspensions, emulsions) or are hardly soluble or easily oxidizable, dosage forms preferably used are soft capsules having a light-shielding shell.

Techniques known for manufacturing soft capsules include the plate method or the rotary method in which two sheet materials for shell formation are punched and shaped into capsules, as well as the in-liquid curing coating method (drop method) in which a solution to be encapsulated and a shell-forming solution are simultaneously dripped into a curing solution through a double nozzle. Soft capsules manufactured by the in-liquid curing coating method are also called seamless soft capsules because of their seamless shell.

When compared to the plate method and the rotary method, the in-liquid curing coating method enables the manufacture of soft capsule formulations having a smaller capsule size (e.g., 2 mm or less), thus also enabling the manufacture of granular soft capsule formulations which are readily taken by children, elderly people, or patients with reduced swallowing ability. Such formulations of smaller size are expected to have improved dispersibility of medicaments in the digestive tract and reduced variations in medicament absorption.

Commonly used soft capsule formulations have a capsule size of about 4 to 20 mm and a shell thickness of about 200 to 600 µm. It is therefore possible to achieve effective light shielding of the encapsulated active ingredient(s) when the shell is supplemented with about 0.1 to 2 wt % of a light-shielding agent, as stated above. However, in conventional techniques, it was inevitable that the shell thickness would be reduced as the capsule size decreased. For this reason, in the case of soft capsule formulations having a capsule size of 2 mm or less, conventional recipes for capsule shell could not ensure a shell thickness enough to provide sufficient light shielding of a light-unstable active ingredient.

As stated above, no soft capsule formulation has been developed for commercial use, which has a small capsule size and sufficiently prevents photodegradation of the encapsulated medicament by the action of a light-shielding shell.

DISCLOSURE OF THE INVENTION

An object of the present invention is to provide a light-stabilized soft capsule formulation, particularly a small-sized light-stabilized soft capsule formulation, which has a shell that ensures effective light shielding of an active ingredient encapsulated thereby.

Another object of the present invention is to provide a method for manufacturing such a light-stabilized soft capsule formulation.

As a result of extensive and intensive efforts directed to recipes for capsule shell of soft capsule formulations and methods for their manufacture, the inventors of the present invention have developed a recipe for capsule shell including a high content of a non-water-soluble light-shielding agent and a technique for its preparation. They also have found that this technique allows a sufficient reduction in light transmittance even for soft capsule shells less than 200 µm in thickness, thus enabling light stabilization of soft capsule formulations containing a light-unstable medicament even with a smaller capsule size. This finding led to the completion of the present invention.

Namely, the present invention provides a light-stabilized soft capsule formulation comprising:
a shell containing a non-water-soluble light-shielding agent and having an average thickness of 200 µm or less; and
a medicament encapsulated by said shell.

In the light-stabilized soft capsule formulation of the present invention, the amount of the non-water-soluble light-shielding agent is preferably 5 to 30 wt %, based on the total amount of all components constituting the shell.

In the light-stabilized soft capsule formulation of the present invention, the non-water-soluble light-shielding agent is preferably titanium oxide.

In the light-stabilized soft capsule formulation of the present invention, the soft capsule formulation preferably has an average capsule size of 2 mm or less.

In the light-stabilized soft capsule formulation of the present invention, the shell is preferably seamless.

In the light-stabilized soft capsule formulation of the present invention, the medicament is preferably a light-unstable substance.

In the light-stabilized soft capsule formulation of the present invention, the medicament is preferably in a liquid form or the medicament is preferably dissolved or suspended in a liquid base.

In the light-stabilized soft capsule formulation of the present invention, the medicament is preferably a vitamin D derivative.

In the light-stabilized soft capsule formulation of the present invention, the major component of the shell is preferably gelatin.

According to another aspect, the present invention provides a method for preparing a shell-forming solution which is used to form a soft capsule shell containing a non-water-soluble light-shielding agent, said method comprising the step of dispersing the non-water-soluble light-shielding agent in a medium free from a gelling agent. Dispersion is preferably accomplished by ultrasonication.

According to yet another aspect, the present invention provides a method for manufacturing a soft capsule formulation containing a non-water-soluble light-shielding agent in its shell, comprising:
(i) the step of preparing a shell-forming solution, comprising the following steps (a) to (c):
   (a) dissolving a gelling agent in Medium A;
   (b) dispersing the non-water-soluble light-shielding agent in Medium B free from the gelling agent; and
   (c) mixing Medium A containing the gelling agent dissolved therein with Medium B containing the non-water-soluble light-shielding agent dispersed therein; and (ii) the step of forming a capsule shell for the soft capsule formulation using the shell-forming solution prepared in the step (i).

In the above step (i), the steps (a) and (b) may be performed in any order or simultaneously. Dispersion in the step (a) is preferably accomplished by ultrasonication.

In the method of the present invention for manufacturing a soft capsule formulation, the step of forming a capsule shell for the soft capsule formulation is preferably accomplished by the in-liquid curing coating method.

The light-stabilized soft capsule formulation of the present invention is preferably manufactured by the method of the present invention for manufacturing a soft capsule formulation.

According to yet another aspect, the present invention provides a unit dose package comprising the light-stabilized soft capsule formulation of the present invention (which is preferably manufactured by the method of the present invention for manufacturing a soft capsule formulation).

According to yet another aspect, the present invention provides a hard capsule, a tablet, an oral solution or an external preparation, which is prepared using the light-stabilized soft capsule formulation of the present invention (which is preferably manufactured by the method of the present invention for manufacturing a soft capsule formulation).

This application claims the priority of Japanese Patent Application No. 2002-134070, the disclosure of which is hereby incorporated by reference in its entirety.

BRIEF DESCRIPTION OF DRAWINGS

FIG. 3 is a graph showing the results of light transmittance measured at each wavelength for the shell sample sheets obtained in Example 1. In the figure, the vertical axis represents the light transmittance of the shell and the horizontal axis represents the detection wavelength. The open diamond denotes a shell sample sheet obtained using a shell-forming solution immediately after its preparation by the in-gelatin dispersion method, the filled diamond denotes a shell sample sheet obtained using a shell-forming solution one hour after its preparation by the in-gelatin dispersion method, the open triangle denotes a shell sample sheet obtained using a shell-forming solution immediately after its preparation by the in-water dispersion method, and the filled triangle denotes a shell sample sheet obtained using a shell-forming solution one hour after its preparation by the in-water dispersion method.

PREFERRED MODE FOR CARRYING OUT THE INVENTION

As used herein, the term "soft capsule formulation" is intended to mean an encapsulated formulation of a medicament, which is encapsulated either alone or in combination with an appropriate excipient, base or the like within a shell component containing an appropriate gelling agent (e.g., gelatin), if necessary together with polyhydric alcohols (e.g., glycerine, sorbitol) or other additives to increase its plasticity, and then shaped into a given form. This term encompasses soft capsule formulations defined in the Japanese Pharmacopoeia 13th revision (JP13) and soft capsule formulations found in USP24, as well as all other concepts such as so-called microcapsules. Such a soft capsule formulation is composed of a substance to be encapsulated (i.e., a medicament, either alone or in combination with a base or the like) and a shell encapsulating the same.

As used herein, the term "medicament" is used as a generic name for substances having specific effects, functions and efficacy. Examples include substances used for the purpose of treating, preventing or diagnosing human or animal diseases (i.e., human or animal drugs), as well as nutrients in foods with health claims and general foods, and animal feed. Other examples include deodorants, insecticides, antimicrobial agents, as well as dyes, pigments and colorants. Thus, the soft capsule formulation of the present invention can also be applied in the fields of pharmaceutical products, agricultural products, sanitary products, as well as office supplies, toys and other industrial products.

A soft capsule is a dosage form useful for obtaining oral formulations of liquid medicaments (e.g., in an oil or suspension form), hardly soluble medicaments, easily oxidizable medicaments, etc. Although soft capsules often encapsulate liquid medicaments, powder and solid medicaments can also be filled in soft capsules when using an appropriate instrument.

As used herein, the term "light-stabilized soft capsule formulation" is intended to mean a soft capsule formulation designed to encapsulate an inherently light-unstable medicament by a capsule shell having a high light-shielding property. Such a formulation is characterized by allowing the medicament encapsulated therein to have improved stability upon light irradiation when compared to the absence of such a light-shielding shell. By taking the form of light-stabilized soft capsule formulations, it is desirable to avoid, to the extent practically acceptable, photochemically induced changes and losses in the physical and chemical properties (e.g., activity, color, smell, taste) of inherently light-unstable medicaments during normal handling, shipping or storage. Light-stabilized soft capsule formulations encompass formulations in the dosage forms of light-stabilized soft capsules, light-stabilized seamless soft capsules, light-stabilized small-sized seamless soft capsules, light-stabilized microcapsules, etc.

Although any medicament can be encapsulated in the soft capsule formulation of the present invention, light-unstable medicaments can be filled to obtain effective light shielding. For example, effective light shielding can be achieved for dihydropyridine derivatives (e.g., nifedipine), antiviral HIV protease inhibitors (e.g., Ritonavir, Saquinavir), therapeutic agents for hyperlipidemia (e.g., clofibrate), iodine compounds (e.g., sodium iopodate, sodium iodide), polyunsaturated fatty acid derivatives (e.g., ethyl eicosapentaenoic acid (EPA), docosahexaenoic acid (DHA)), carotenoids (e.g., lycopene, bixin, β-carotene, xanthophyll, lutein), ubiquinones (coenzyme Q) (e.g., ubidecarenone used as a metabolizable cardiac stimulant), various vitamin derivatives, as well as indomethacin, colchicine, diazepam, syrosingopine, norethisterone, piretanide, propericyazine, perphenazine, mequitazine, medazepam, menatetrenone, indenolol hydrochloride, reserpine, sofalcone, bromocriptine mesilate, bufetolol hydrochloride and oxprenolol hydrochloride when they are filled into the soft capsule formulation of the present invention.

Among vitamin derivatives, fat-soluble ones are preferred for use. Examples include vitamin A derivatives (e.g., tretinoin, liver oil, retinol palmitate), vitamin A analogs (e.g., etretinate), vitamin D derivatives, vitamin E derivatives (e.g., tocopherol nicotinate, tocopherol acetate, tocopherol calcium succinate), and vitamin K derivatives (e.g., phytonadione (vitamin K1), menaquinone (vitamin K2), menadione (vitamin K3), menatetrenone, phytonadione).

The term "vitamin D derivative" refers to a compound having a 9,10-secoandrostan skeleton, which may have, in addition to the 3-position hydroxy group, an additional hydroxy group at the 1-position or an optionally hydroxy-substituted alkyl side chain at the 17- or 2-position. Alternatively, the 26- or 27-position hydrogen atom may be replaced by a fluorine atom. In this way, the vitamin D derivative may have a substituent(s) on its alkyl side chain and its basic skeleton. Specific examples include vitamin $D_2$ derivatives (ergocalciferol derivatives) and vitamin $D_3$ derivatives (cholecalciferol derivatives).

More specific examples of vitamin $D_3$ derivatives include 1α-hydroxyvitamin $D_3$, 24-hydroxyvitamin $D_3$, 25-hydroxyvitamin $D_3$, 1α,24-dihydroxyvitamin $D_3$, 1α,25-dihydroxyvitamin $D_3$, 24,25-dihydroxyvitamin $D_3$, 1α,24,25-trihydroxyvitamin $D_3$, 1α,25-dihydroxy-22-oxavitamin $D_3$, 1α,25-dihydroxy-2β-(3-hydroxypropoxy) vitamin $D_3$, and 1α,25-dihydroxy-26,26,26,27,27,27-hexafluorovitamin $D_3$.

A medicament as an active ingredient can be filled into the soft capsules of the present invention, either alone or in combination with any base or excipient. Any type of base, either fat-soluble or water-soluble, can be used as long as it does not impair the medicament's activity and does not affect various physical properties of the soft capsule shell, such as strength, gas permeability, and pH- and time-dependent or -independent disintegration/dissolution profiles. Likewise, the base per se may be in a liquid or solid state at normal temperature as long as it can be filled into capsules with the help of heating or dilution with other solvents, etc. Examples of such a base include vegetable oils (e.g., soybean oil, sesame oil, cottonseed oil, olive oil), fatty acid glycerides (e.g., medium chain triglycerides), propylene glycol, propylene glycol fatty acid esters, polyethylene glycol, polyvinylpyrrolidone, triacetin, liquid paraffin, polyoxyethylene sorbitan fatty acid esters, sucrose fatty acid esters, ethanol and purified water, which may be used alone or in combination. Bases preferred for dissolving fat-soluble medicaments such as vitamins A, D, E and K are vegetable oils or fatty acid glycerides, with medium chain triglycerides being particularly preferred. In the case of using a water-soluble base, it is preferable to provide a protection layer between the shell layer and the medicament layer in consideration of influences on the capsule shell.

A medicament to be filled into the soft capsule shell of the present invention is preferably exemplified by, but not limited to, those in a liquid form or those dissolved, suspended or emulsified in such a base as listed above. The medicament may also be in a solid form (e.g., powders, granules) or in a semi-solid form (e.g., creams).

The soft capsule formulation of the present invention preferably has a capsule size of 2 mm or less. In the present invention, such a capsule formulation is referred to as a small-sized soft capsule formulation, the concept of which includes a part of so-called microcapsules. The small-sized soft capsule formulation of the present invention has a capsule size of 2000 µm or less, preferably 1500 µm or less, more preferably 1200 µm or less, even more preferably 1000 µm or less, and most preferably 700 µm or less. At the same time, it preferably has a capsule size of at least 50 µm, more preferably at least 100 µm, even more preferably at least 200 µm, still more preferably at least 400 µm, and most preferably at least 500 µm. More specifically, the capsule size ranges from 50 to 2000 µm, preferably 100 to 1500 µm, more preferably 200 to 1200 µm, even more preferably 400 to 1000 µm, and most preferably 500 to 700 µm. Small-sized soft capsule formulations having such a capsule size can be manufactured, e.g., by the in-liquid curing coating method using a commercially available manufacturing machine (e.g., SPHEREX-Labo (Freund Corporation)). They can also be manufactured according to known processes for microcapsule preparation, such as coacervation, phase separation, interfacial polymerization, in-situ polymerization and in-liquid drying.

As used herein, the "capsule size" of the soft capsule formulation is intended to mean the outer diameter of the soft capsule formulation, as determined by selecting any one soft capsule and measuring its size either at any single point or at several points, preferably at 3 points, more preferably at 5 points, to calculate an average capsule size. Further, it is most preferable to repeat the same measurement for several soft capsules, preferably at least 5 capsules, more preferably at least 10 capsules, to calculate an average capsule size.

The soft capsule formulation of the present invention may take any form, but it preferably takes the form of spheres, ellipsoids, etc. Also, the soft capsule formulation of the present invention is preferably of seamless type with a seamless shell.

The soft capsule formulation of the present invention preferably has a shell thickness of 200 µm or less. The term "shell thickness" is used to mean the cross-sectional capsule wall thickness of the soft capsule formulation. In general, to measure the cross-sectional capsule wall thickness, soft capsule formulations of elliptical form may be cut along their minor axis, while soft capsule formulations of spherical form may be cut in any direction through the center. The measurement may be accomplished by using the cross-section of a single soft capsule to obtain the shell thickness reflecting the whole cross-section. For example, two points with maximum and minimum thicknesses may be measured and averaged. Preferably, three points with maximum, minimum and average thicknesses may be measured and averaged. More preferably, any five points including those with maximum and minimum thicknesses may be measured and averaged. It is further desirable to repeat the same measurement for several soft capsules, preferably at least 5 capsules, more preferably at least 10 capsules, to calculate an average shell thickness.

In the soft capsule formulation of the present invention, the major component of the shell is a gelling agent including gelatin and agar, which may be used alone or in combination. Examples of gelatin available for use include acid-treated gelatin, alkali-treated gelatin, as well as chemically modified gelatin such as succinylated gelatin. The shell of the soft capsule formulation may be supplemented with a known plasticizer such as glycerine, sorbitol, mannitol or polyethylene glycol. Likewise, for the purpose of controlling various physical properties of the shell (e.g., strength, gas permeability, pH- and time-dependent or -independent disintegration/ dissolution profiles) or avoiding time-dependent changes in these properties, the shell may also be blended at any ratio with one or more additives including carrageenan, gellan gum, xanthan gum, gum arabic, locust bean gum, alginic acid, sodium alginate, dextrin and pullulan.

In addition to these materials, any type of additive may be incorporated into either the capsule shell or the capsule contents, if necessary. For example, it is possible to incorporate one or more members selected from colorants (e.g., caramel, β-carotene, tar dyes), antiseptics (e.g., methylparaben, ethylparaben, propylparaben), antioxidants or stabilizers (e.g., BHT, BHA, tocopherol, gallic acid, propyl gallate, ascorbic acid, sodium ascorbate, ascorbyl stearate ester), thickeners or dispersants (e.g., fatty acid monoglycerides, beeswax), and solvents or solvent aids (e.g., ethanol, ethyl acetate, surfactants).

The soft capsule shell preferably has a water content of at least 1 wt %, more preferably at least 5 wt %, and most preferably at least 7 wt %. At the same time, it preferably has a water content of 20 wt % or less, more preferably 15 wt % or less, and most preferably 13 wt % or less. More specifically, the water content ranges from 1 to 20 wt %, preferably 5 to 15 wt %, and most preferably 7 to 13 wt %.

It should be noted that substances used as capsule shell components are preferably free from any risk of impairing the activity of capsule contents (a medicament to be encapsulated and/or its base, etc.). For example, it is preferable to avoid the use of substances that readily react with capsule contents.

The light-stabilization effect on the encapsulated medicament provided by the light-stabilized soft capsule formulation of the present invention may be evaluated as follows. A certain medicament is formulated into a light-stabilized soft capsule formulation, while its contents alone (including the medicament) is provided as a control. These two samples are stored under certain irradiation conditions and compared for % reduction in active ingredient content (100%–remaining %) before and after storage. In this case, the capsule contents used as a control may be extracted from the inside of the prepared light-stabilized soft capsule formulation or may be a sample newly prepared to have the same composition as the contents of the soft capsule formulation. Alternatively, a certain medicament is formulated into both a light-stabilized soft capsule formulation and a soft capsule formulation free from a light-shielding agent (control), which has the same composition as the light-stabilized soft capsule formulation, except that its shell contains no light-shielding agent. These two samples are stored under certain irradiation conditions and compared for % reduction in active ingredient content (100%–remaining %) before and after storage. If the % reduction in active ingredient content is significantly lower in the light-stabilized soft capsule formulation than in the control sample, it indicates that the test formulation achieves light stabilization. Irradiation conditions may be set to, for example, an accumulated illumination of 600,000 lux×hour (lux·hr) or 1,200,000 lux·hr using a white fluorescent lamp, or an accumulated radiation energy of 200 W·h/m$^2$ using a near-ultraviolet fluorescent lamp, or a combination thereof. Alternatively, the samples may also be evaluated by the quantity of degraded products generated during storage, instead of comparing % reduction in medicament content before and after storage. In this case, if the quantity of degraded products is significantly lower in the light-stabilized soft capsule formulation than in the control sample, it indicates that the test formulation achieves light stabilization.

The non-water-soluble light-shielding agent used in the present invention ensures prevention of light penetration when incorporated into the soft capsule shell. As used herein, the term "non-water-soluble" is intended to mean that the amount of water required to dissolve 1 g of the light-shielding agent is 100 mL or more. Specific examples include metal oxides (e.g., titanium oxide, iron sesquioxide (iron oxide red), yellow iron sesquioxide, yellow iron oxide, zinc oxide), inorganic compounds (e.g., talc, calcium carbonate, magnesium carbonate, magnesium silicate, light anhydrous silicic acid), and food colors (e.g., food red #3 aluminum lake, food yellow #4 aluminum lake, food yellow #5 aluminum lake, food green #3 aluminum lake, food blue #2 aluminum lake, sodium copper chlorophyllin). In the present invention, these non-water-soluble light-shielding agents may be used alone or in combination. To obtain a high light-shielding effect, it is preferable to use metal oxides, with titanium oxide (titanium dioxide: $TiO_2$) being particularly preferred for use. Titanium oxide used in the present invention may be commercially available, either of anatase or rutile type.

In general, titanium oxide having an average particle size of 0.2 to 0.4 μm is widely used, but there is no limitation on the particle size of titanium oxide to be used in the present invention. In order to obtain a higher light-shielding effect, titanium oxide having an average particle size less than 0.2 μm may also be used.

To ensure a light-stabilization effect even with a thinner soft capsule shell, the content of a non-water-soluble light-shielding agent is preferably at least 5 wt %, more preferably 10 wt %, and even more preferably at least 15 wt %, based on the total amount of all components constituting the shell (including the weight of the non-water-soluble light-shielding agent), which is set to 100%. On the other hand, in a case where a light-shielding agent is added in an amount exceeding 30 wt %, there will be a tendency to reduce both the formability of capsule shell and the strength of the resulting formulation. For this reason, the content of a non-water-soluble light-shielding agent is preferably 30 wt % or less, more preferably 25 wt % or less, and most preferably about 20 wt %. More specifically, it ranges from 5 to 30 wt %, preferably 10 to 25 wt %, and most preferably 15 to 20 wt %. It should be noted that the phrase "total amount of all components constituting the shell" as used herein refers to the sum of the amounts of all capsule shell components, except for liquid (i.e., water and volatile media) added to prepare a shell-forming solution. For example, in Examples 1 to 3 described later, the total amount of all components constituting the shell refers to the sum of all components except for "purified water" shown in the recipes for shell-forming solutions, i.e., the sum of the weights of "gelatin", "D-sorbitol" and "titanium oxide." All the components constituting the shell are not necessarily required to be in a solid state at normal temperature. For example, hydrous components such as glycerine are also among the capsule shell components. In this case, the amount of a capsule shell component derived from glycerine is defined as the weight of glycerine in a hydrous state used during formulation.

To incorporate a desired amount of a non-water-soluble light-shielding agent into the soft capsule shell, the content of the non-water-soluble light-shielding agent may be adjusted relative to the total amount of all components constituting the shell. For example, to obtain a soft capsule shell containing 10 wt % of a non-water-soluble light-shielding agent, a shell-forming solution may be prepared in such a way as to give a 90:10 ratio of the total amount of other capsule shell components (except for water and volatile media added to prepare the shell-forming solution) to the amount of the non-water-soluble light-shielding agent.

Moreover, to increase the light-stabilization effect of a non-water-soluble light-shielding agent, the light-shielding agent is preferably distributed as uniformly as possible over the shell. In other words, the light-shielding agent is preferably in a state as near as possible to primary particles with fewer particle aggregates. Primary particles are unit particles constituting a secondary particle, while a secondary particle is a term used to describe a state in which fine particles of titanium oxide or the like are present as aggregates in gas or liquid environments. Thus, primary particles are smaller than fine particles in an aggregated form usually found in gas or liquid environments.

In order that a certain non-water-soluble light-shielding agent is examined for the relationship of its content and the shell thickness with the resulting light-stabilization effect, for example, shell sample sheets with different thicknesses and different contents of the non-water-soluble light-shielding agent may be prepared and measured for their light-shielding effect, as described in the Example section below. Alternatively, various types of soft capsule formulations may be actually manufactured to have different shell thicknesses and different contents of the non-water-soluble light-shielding agent, followed by measuring the percentage of remaining medicament, etc.

Although the light-stabilized soft capsule formulation of the present invention is preferably manufactured using, but not limited to, the in-liquid curing coating method, any method can be used for this purpose as long as it allows the manufacture of the light-stabilized soft capsule formulation of the present invention. Examples include the plate method, the rotary method, in-air suspension coating, interfacial polymerization, in-situ polymerization, phase separation, in-liquid drying, electrostatic coalescence, spray drying granulation, spray chilling, core replacement, the powder bed method, cold encapsulation, vacuum deposition coating, and dry impact blending.

The in-liquid curing coating method, which is also called the drop method, relies on the basic principle that capsules are formed with the help of interfacial tension between mutually immiscible liquids. For example, using a concentric double nozzle, an oily drug solution containing a medicament and an aqueous shell-forming solution may be simultaneously dripped through the center and outer nozzles, respectively, into an oily curing solution to give spherical capsules retaining the double structure composed of an inner layer of the drug solution and an outer layer of the shell-forming solution. Techniques based on this principle are collectively called the drop method. For example, the drop method can also be used for manufacturing single-layer or multi-layer capsules, non-spherical capsules, capsules having a medicament-containing shell, and capsules encapsulating a hydrophilic base. Procedures used for dripping are not limited in any way. The nozzle is not necessarily made to come into contact with the surface of the curing solution, i.e., may be placed either in the air or in the curing solution. An encapsulation machine for soft capsule formulations, which is based on the above principle, is also called a Globex-type capsulator. Soft capsule formulations filled by the drop method may be subjected to further steps (e.g., drying), if necessary.

The concentration of a shell-forming solution=(total amount of all components constituting the shell)/(total amount of all components constituting the shell+amount of water or volatile media added to prepare the shell-forming solution) may be selected in consideration of the formability of capsules. For example, to prepare capsules having a 4:6 weight ratio of shell to content (40% shell) by the in-liquid curing coating method, although the required concentration of a shell-forming solution may be determined in consideration of the formability of capsules, a 25 wt % shell-forming solution may be used for encapsulation at the following ratio: weight of the shell-forming solution/weight of capsule contents=16/6, or alternatively, a 40 wt % shell-forming solution may be used for encapsulation at the following ratio: weight of the shell-forming solution/weight of capsule contents=10/6. In either case, soft capsule formulations with 40% shell ratio can be obtained after a drying step. It should be noted that the weight of the shell-forming solution includes the weight of water or volatile media added to prepare the shell-forming solution.

To reduce deviations in the light-shielding effect of the shell among the manufactured soft capsule formulations, it is necessary to keep uniform dispersion of a non-water-soluble light-shielding agent in a shell-forming solution from beginning to end of encapsulation. In other words, it is important to keep a non-water-soluble light-shielding agent from easily settling out for a period during which a shell-forming solution is in a tank of an encapsulation machine. In manufacturing aspects, it is therefore preferred that a non-water-soluble light-shielding agent is kept from easily settling out and can be maintained in a dispersed state at least during encapsulation after preparation of a shell-forming solution. The time required for encapsulation will vary depending on the manner and the scale of encapsulation to be used, but it is desirable to maintain a given state of dispersion for at least 1 hour or more, preferably 3 hours or more, by taking into account the time required to adjust machine settings before encapsulation.

To disperse a non-water-soluble light-shielding agent in a shell-forming solution, known mixers (e.g., a propeller mixer, a homomixer) can be used, but ultrasonication is preferred to achieve more uniform dispersion. For example, a commercially available ultrasonic cleaner can be used for this purpose. However, in a case where a non-water-soluble light-shielding agent is incorporated at a high content, as in the present invention, it has been found that it is difficult to ensure successful dispersion from beginning to end of encapsulation even when the non-water-soluble light-shielding agent is added to a solution of a gelling agent (e.g., gelatin) and then treated by ultrasonication. The inventors of the present invention made an attempt to disperse a non-water-soluble light-shielding agent in water, e.g., by ultrasonication before being added to a solution of a gelling agent. As a result, they have found that even in the case of incorporating a large amount of a non-water-soluble light-shielding agent, it is possible to ensure successful dispersion until the end of encapsulation and hence make soft capsule formulations having a good light-shielding property without any variation among capsules.

In the present invention, such a method for preparing a shell-forming solution is referred to as the in-water dispersion method, which is characterized in that a non-water-soluble light-shielding agent is dispersed in water and then added to a solution of a gelling agent. A non-water-soluble light-shielding agent may be dispersed in water according to standard procedures, e.g., using a mixer, but ultrasonication is more preferred for this purpose. As used herein, the term "in-water" of the in-water dispersion method is intended to mean a medium free from a gelling agent, which includes cases where a non-water-soluble light-shielding agent is dispersed not only in pure water, but also in an aqueous solution supplemented with additives such as plasticizers, colorants, solvents, solvent aids, dispersants, solubilizers, stabilizers, correctives, sweeteners, adsorbents, abherents, antioxidants, antiseptics, preservatives, desiccants, flavors, perfumes, pH adjusters, binders, disintegrating agents, release-controlling agents, etc. These additives may be water-soluble or non-water-soluble. Examples of non-water-soluble additives include antiseptics such as methyl parahydroxybenzoate, ethyl parahydroxybenzoate, propyl parahydroxybenzoate, butyl parahydroxybenzoate, isobutyl parahydroxybenzoate, isopropyl parahydroxybenzoate, benzyl parahydroxybenzoate and sorbic acid.

Shell-forming solutions prepared using this in-water dispersion method can maintain a given state of dispersion during the time required for encapsulation, even when containing a high content of a non-water-soluble light-shielding agent. The amount of water or an aqueous solution required to disperse a non-water-soluble light-shielding agent therein is preferably at least 100 wt %, more preferably at least 300 wt %, based on the weight of the non-water-soluble light-shielding agent. It is also preferably 10000 wt % or less, and more preferably 5000 wt % or less. The amount of water used to dissolve a gelling agent will vary depending on the type of base to be used, but it is usually at least 80 wt %, more preferably at least 200 wt %, based on the weight of the gelling agent. It is also preferably 5000 wt % or less, and more preferably 1000 wt % or less. The frequency of ultrasonic waves to be used will vary depending on the type and amount of non-water-soluble light-shielding agent to be used, but it is usually at least 10 kHz, and more preferably at least 20 kHz. It is also 500 kHz or less, and more preferably 60 kHz or less. More specifically, it ranges from 10 kHz to 500 kHz, and preferably 20 kHz to 60 kHz. The time for ultrasonication is preferably at least 10 seconds, more preferably at least 30 seconds, and even more preferably at least 1 minute. It is also preferably 24 hours or less, more preferably 10 hours or less, and most preferably 30 minutes or less. More specifically, it ranges from 10 seconds to 24 hours, preferably 30 seconds to 10 hours, even more preferably 30 seconds to 1 hour, and most preferably 1 minute to 30 minutes.

The degree of dispersion of a non-water-soluble light-shielding agent in a shell-forming solution may be evaluated by measurement using a particle size distribution analyzer, sedimentation velocity measurement, microscopic observation, etc. In the case of aiming at light shielding, as in the present invention, the degree of dispersion may be evaluated by light transmittance measurement.

The light-stabilized soft capsule formulation of the present invention may be fabricated into various dosage forms. For example, the light-stabilized soft capsules of the present invention may be further be treated to have some coating on it. Alternatively, the light-stabilized soft capsule formulation of the present invention may be filled into hard capsules. Moreover, the light-stabilized soft capsule formulation of the present invention may be compressed and molded into a certain dosage form together with an appropriate additive(s) or may be shaped and dried in a certain mold together with an additive(s) wetted with an appropriate medium, thereby giving tablets. Also, the light-stabilized soft capsule formulation of the present invention may be incorporated into oral solutions or external preparations. In each case of these fabrication examples, light-stable formulations can be obtained when using the light-stabilized soft capsule formulation of the present invention.

Moreover, in each case of these fabrication examples, it is possible to use one or more light-stabilized soft capsule formulations according to the present invention. Namely, a combination drug can be manufactured if the above fabrications are conducted using several types of light-stabilized soft capsules containing different active ingredients. In this case, since individual medicaments are each protected by the capsule shell, this not only ensures light stabilization, but also avoids interactions among medicaments, as exemplified by degradation. Likewise, sustained release formulations and long-acting formulations can be manufactured if the above fabrications are conducted using several types of capsules which contain the same active ingredient, but are designed to have different dissolution profiles by changing their capsule size, shell thickness, recipes, etc. In this case, it is possible not only to ensure light stabilization of the medicament, but also to design formulations capable of optionally controlling the release profile of the medicament.

The light-stabilized soft capsule formulation of the present invention may be packaged in containers (e.g., bottles), either directly or in various dosage forms after fabrication. It may also be packaged into unit dose packages containing a single dose per package. More specifically, blister packaging such as PTP (press through package) or other packaging such as SP (strip package) may be used for this purpose. Alternatively, the light-stabilized soft capsule formulation may be divided and packaged in the form of three-sided seal packages, four-sided seal packages, stick packages, etc. To exclude moisture, materials with low moisture permeability are desirably selected for use in these packages. To obtain further increases in light-shielding effect, it is also preferable to impart an additional light-shielding effect to these packages per se.

EXAMPLES

The present invention will be further described in the following examples, which are not intended to limit the scope of the invention.

In the following examples, the products shown below were used:

Gelatin: acid-treated gelatin, APB-H, Nitta Gelatin Inc.
D-sorbitol: DM-50, Towa Chemical Industry Co., Ltd.
Titanium oxide: A-100, Ishihara Sangyo Kaisha, Ltd.
MCT: medium chain triglyceride ODO, The Nisshin Oil Mills, Ltd.
Absolute ethanol: pharmacopeial grade, Wako Pure Chemical Industries, Ltd.

Example 1

Evaluation of Dispersibility and Light Transmittance for Titanium Oxide-Containing Shell-Forming Solutions Prepared by in-Water Dispersion Method (1) Preparation of a Titanium Oxide-Containing Shell-Forming Solution by in-Water Dispersion Method According to Recipe 1 shown below, a shell-forming solution (1000 g) was prepared by the in-water dispersion method. The total amount of all components constituting the shell was set to 25 wt % of the shell-forming solution, and the content of titanium oxide was set to 10 wt % of the total amount of all components constituting the shell.

(Recipe 1)

| | |
|---|---|
| Gelatin | 20.0 wt % |
| D-sorbitol | 2.5 wt % |
| Titanium oxide | 2.5 wt % |
| Purified water | 75.0 wt % |

Procedures for preparing the shell-forming solution are as follows. D-sorbitol (25 g) and gelatin (200 g) were dissolved in hot water at 80° C. or more (500 mL) to prepare Solution A. Titanium oxide (25 g) was ground in a mortar and added to purified water (100 mL), followed by ultrasonication at 47 kHz for 10 minutes (BRANSONIC ULTRASONIC CLEANER, Model 5210 J-DTH, Emerson Japan, Ltd.) while stirring by hand to prepare a suspension (Solution B) Next, the whole of Solution B was passed through a 100 mesh sieve and then added to Solution A. Further, titanium oxide remaining in the Solution B vessel (beaker) was washed with purified water (150 mL), which was also passed through a 100 mesh sieve and then added to Solution A. The resulting suspension was stirred by hand to prepare a shell-forming solution.

(2) Preparation of a Titanium Oxide-Containing Shell-Forming Solution by in-Gelatin Dispersion Method For comparison purposes, the same recipe as show in (1) above was used to prepare a shell-forming solution by the in-gelatin dispersion method.

Procedures for preparing a shell-forming solution by the in-gelatin dispersion method are as follows. D-sorbitol (25 g) and gelatin (200 g) were dissolved in hot water at 80° C. or more (500 mL) to prepare Solution A. Titanium oxide (25 g) ground in a mortar was added to a beaker containing 100 mL purified water and then stirred by hand to prepare Solution B. Next, the whole of Solution B was passed through a 200 mesh sieve and then added to Solution A. Further, titanium oxide remaining in the Solution B vessel (beaker) was washed with purified water (150 mL), which was also passed through a 200 mesh sieve and then added to Solution A. The resulting mixture (suspension) was subjected to ultrasonication at 47 kHz for 1 hour (BRANSONIC ULTRASONIC CLEANER, Model 5210 J-DTH, Emerson Japan, Ltd.) in a hot water bath at 60° C. or more, and then stirred by hand to prepare a shell-forming solution.

(3) Evaluation of Dispersibility for Titanium Oxide in Shell-Forming Solutions

To confirm the dispersed state of titanium oxide in shell-forming solutions, part of the shell-forming solutions prepared in (1) and (2) above were each taken into a petri dish and observed under a microscope for the dispersed state of titanium oxide. When compared to the shell-forming solution prepared by the in-gelatin dispersion method, the shell-forming solution prepared by the in-water dispersion method clearly contained fewer titanium oxide aggregates (observed as white massive products) and ensured a good dispersed state of titanium oxide.

(4) Evaluation of Light Transmittance for Capsule Shell

For the purpose of evaluating the light-shielding effect of titanium oxide, the shell-forming solutions prepared in (1) and (2) above were used to prepare shell sample sheets with a film thickness of 0.12 to 0.17 mm. The resulting sample sheets were measured for their light transmittance using a visible-ultraviolet spectrophotometer (SPECTROPHO-TOMETER, DU640, BECKMAN).

Figure 1:
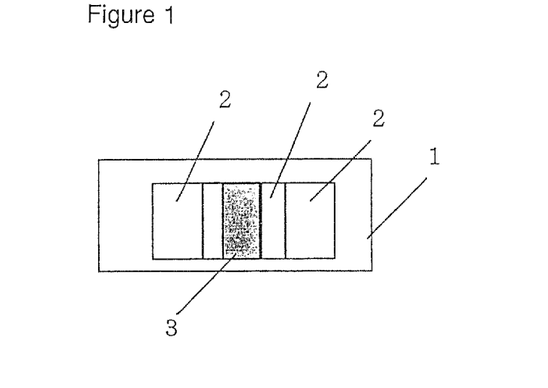
FIG. 1 is a top view of the mold used in Examples 1 and 2 for preparing a shell sample sheet.
Figure 2:
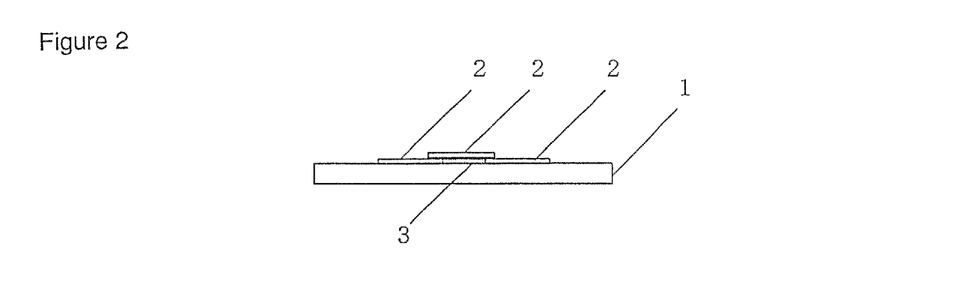
FIG. 2 is a side view of the mold shown in FIG. 1 for preparing a shell sample sheet.

As shown in FIGS. 1 and 2, the sample sheets were prepared by pouring each shell-forming solution into a mold constructed from three cover glasses (MICRO COVER GLASS, MATSUNAMI GLASS) and cooling the same at 5° C. for 3 hours. FIG. 1 is a top view of the mold containing a sample sheet, while FIG. 2 is a side view of the mold.

In FIGS. 1 and 2, 1 represents a slide glass with a thickness of 0.9 to 1.2 mm (MICRO SLIDE GLASS, 75×25 mm, MATSUNAMI GLASS), 2 represents a cover glass with a thickness of 0.12 to 0.17 mm (MICRO COVER GLASS, 18×18 mm, MATSUNAMI GLASS), and 3 represents a shell sample sheet.

For each shell-forming solution, three and two shell sample sheets were prepared immediately and one hour, respectively, after the preparation of the shell-forming solution, as described below.

A shell-forming solution was prepared in the manner shown in (1) above and immediately poured into a mold to give three shell sample sheets. The thus prepared shell-forming solution was also transferred to a shell-forming solution storage vessel (jacket) of an encapsulation machine (SPHEREX-Labo (SPX-LABO), Freund Corporation) and stirred at 70° C. for 1 hour with a stirrer, followed by collecting the shell-forming solution from the middle and upper parts of the vessel. Two shell sample sheets were prepared, one of which was prepared from the shell-forming solution collected from the middle part of the vessel, and the other of which was prepared from the shell-forming solution collected from the upper part of the vessel.

A shell-forming solution prepared as shown in (2) above was also used to prepare sample sheets in the same manner.

Each shell sample sheet was mounted on a cell holder of a visible-ultraviolet spectrophotometer and measured for its absorbance between 350 and 300 nm to calculate light transmittance according to the following equation found in JP13.

$$\text{Light transmittance } (\%) = \frac{1}{10^A} \times 100$$

A: Absorbance

In the case of the sample sheets prepared immediately after the preparation of each shell-forming solution, the light transmittance was averaged over three sample sheets. In the case of the sample sheets prepared one hour after the preparation of each shell-forming solution, the light transmittance was averaged over two sample sheets, one of which was prepared from the shell-forming solution collected from the middle part of the vessel, and the other of which was prepared from the shell-forming solution collected from the upper part of the vessel.

Figure 3:
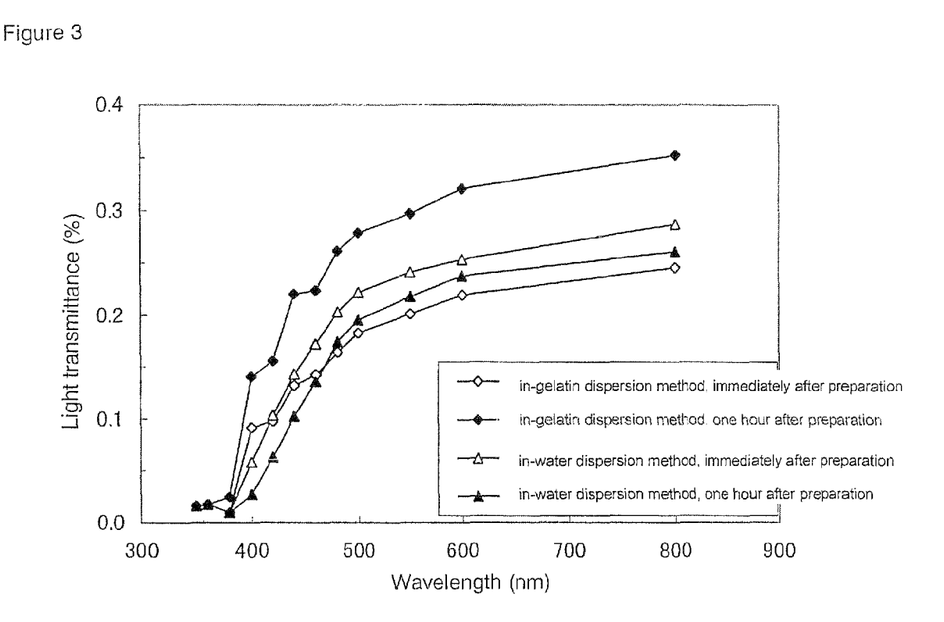

FIG. 3 shows the results obtained. As shown in the figure, the light transmittance was the same between the sample sheets prepared immediately after the preparation of the shell-forming solutions by both methods, the in-gelatin dispersion method and the in-water dispersion method. In the case of the shell-forming solution obtained by the in-water dispersion method, the light transmittance was almost the same between the sample sheets prepared immediately and the ones prepared one hour after the preparation of the shell-forming solution. However, in the case of the shell-forming solution obtained by the in-gelatin dispersion method, the light transmittance was clearly increased in the sample sheets prepared one hour after the preparation of the shell-forming solution, as compared to the sample sheets prepared immediately after the preparation of the shell-forming solution.

These results indicated that the in-gelatin dispersion method permitted the preparation of a shell-forming solution in which a high concentration of titanium oxide was dispersed, but the dispersed state of titanium oxide became insufficient with the passage of time after preparation. Thus, the use of a shell-forming solution prepared by the in-gelatin dispersion method may cause differences in light stability between capsule formulations manufactured at the beginning of encapsulation and those manufactured at the middle or late stage of encapsulation. In contrast, when using the in-water dispersion method, titanium oxide attains better dispersibility and, as shown in FIG. 3, does not easily settle out even with the passage of time. Thus, capsule formulations of uniform quality can be manufactured even by using a shell-forming solution having a high content of titanium oxide.

Example 2

Effects of Titanium Oxide Content and Shell Thickness on Light Transmittance To confirm differences in light-shielding effect caused by different titanium oxide contents, shell-forming solutions were prepared according to the following three recipes such that the content of titanium oxide in the total amount of all components of the shell formed from the shell-forming solutions were 4 wt %, 10 wt % and 20 wt % titanium oxide, respectively.

(Recipe 2-1) 4 Wt % Titanium Oxide in the Shell

| | |
|---|---|
| Gelatin | 21.5 wt % |
| D-Sorbitol | 2.5 wt % |
| Titanium oxide | 1.0 wt % |
| Purified water | 75.0 wt % |

(Recipe 2-2) 10 Wt % Titanium Oxide in the Shell

| | |
|---|---|
| Gelatin | 20.0 wt % |
| D-sorbitol | 2.5 wt % |
| Titanium oxide | 2.5 wt % |
| Purified water | 75.0 wt % |

(Recipe 2-3) 20 Wt % Titanium Oxide in the Shell

| | |
|---|---|
| Gelatin | 17.5 wt % |
| D-sorbitol | 2.5 wt % |
| Titanium oxide | 5.0 wt % |
| Purified water | 75.0 wt % |

The three shell-forming solutions prepared according to the above recipes were used to prepare shell sample sheets with a film thickness of 0.12-0.17 mm or 0.9-1.2 mm, and the light transmittance was measured for each sample sheet for the purpose of confirming the relationship between shell thickness and light-shielding effect.

The shell-forming solutions were prepared as shown in Example 1(1). Three shell sample sheets were prepared in the manner shown in Example 1(4) from each shell-forming solution immediately after its preparation. The light transmittance was measured and averaged over the sheets. It should be noted that to prepare shell sample sheets with a film thickness of 0.9 to 1.2 mm, slide glasses of 0.9 to 1.2 mm thickness were used instead of the cover glasses in the mold shown in FIGS. 1 and 2.

Figure 4:
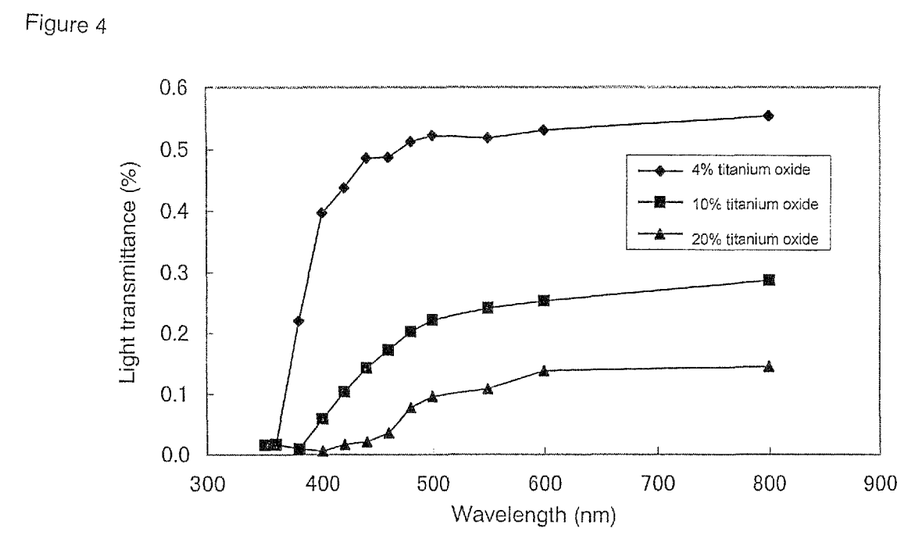
FIG. 4 is a graph showing the results of light transmittance measured at each wavelength for the shell sample sheets obtained in Example 2. In the figure, the vertical axis represents the light transmittance of the shell and the horizontal axis represents the detection wavelength. The filled diamond, filled square and filled triangle denote shell sample sheets obtained using shell-forming solutions containing 4%, 10% and 20% titanium oxide, respectively.
Figure 5:
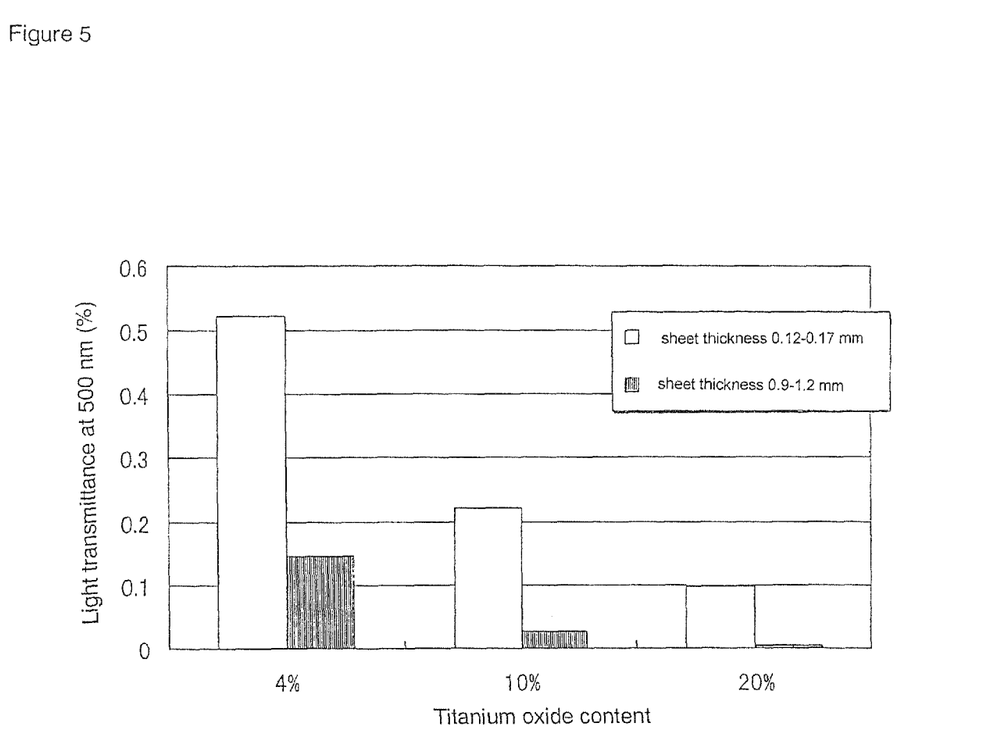
FIG. 5 is a graph showing the relationship among titanium oxide content, sheet thickness and light transmittance at 500 nm of the shell sample sheets obtained in Example 2.

FIGS. 4 and 5 show the results of light transmittance measurement. As shown in FIG. 4, in the wavelength range longer than 350 nm, the light transmittance decreased with increase in titanium oxide content. As shown in FIG. 5, the light transmittance significantly decreased with increase in shell thickness at each titanium oxide content.

These results indicated that even in the range of 4% to 20% titanium oxide content which was higher than that commonly used (around 0.1-2%), there was no minimum limit for light transmittance and a higher titanium oxide content in capsule shell produced a higher light-shielding effect. It was also indicated that increased shell thickness produced a higher light-shielding effect.

Example 3

Light-Stabilization Effect of Soft Capsule Formulations

Four soft capsule formulations having different titanium oxide contents in their soft capsule shell were manufactured by the in-liquid curing coating method and evaluated for their light stability.

(1) Preparation of Soft Capsule Formulations

The following materials were used as the contents of soft capsule formulations: 0.0017 wt % 1α-hydroxyvitamin $D_3$ ((5Z,7E)-9,10-secocholesta-5,7-10(19)-triene-1α,3β-diol), 100 wt % MCT, and 5.0 wt % absolute ethanol. 1α-Hydroxyvitamin $D_3$ was dissolved in absolute ethanol and MCT was then added thereto, followed by hand stirring to prepare a solution to be encapsulated. The resulting solution was sealed in a container and stored in a cool dark place (10° C.) until use.

The following four recipes were employed for preparation of shell-forming solutions such that the content of titanium oxide was 0 wt %, 5 wt %, 10 wt % or 20 wt %, based on the total amount of all components constituting the shell.

(Recipe 3-1) 0 Wt % Titanium Oxide

| | |
|---|---|
| Gelatin | 22.5 wt % |
| D-sorbitol | 2.5 wt % |
| Purified water | 75.0 wt % |

(Recipe 3-2) 5 Wt % Titanium Oxide

| | |
|---|---|
| Gelatin | 21.25 wt % |
| D-sorbitol | 2.5 wt % |
| Titanium oxide | 1.25 wt % |
| Purified water | 75.0 wt % |

(Recipe 3-3) 10 Wt % Titanium Oxide

| | |
|---|---|
| Gelatin | 20.0 wt % |
| D-sorbitol | 2.5 wt % |
| Titanium oxide | 2.5 wt % |
| Purified water | 75.0 wt % |

(Recipe 3-4) 20 Wt % Titanium Oxide

| | |
|---|---|
| Gelatin | 17.5 wt % |
| D-sorbitol | 2.5 wt % |
| Titanium oxide | 5.0 wt % |
| Purified water | 75.0 wt % |

Each shell-forming solution was prepared in accordance with Example 1(1) and corrected for the weight of evaporated water. The containers were sealed and stored overnight in a thermostatic chamber at about 60° C. until use. Soft capsule formulations were manufactured using a SPHEREX-Labo (SPX-LABO, Freund Corporation).

Each shell-forming solution was stirred by hand and then charged into a shell-forming solution storage jacket of the SPHEREX-Labo. After the jacket temperature was set to give a solution temperature of about 50° C., the shell-forming solution was degassed.

The solution to be encapsulated was charged into a drug solution tank, followed by encapsulation. The encapsulation required about 2 to 3 hours. The resulting soft capsules were dried at 20° C. to 30° C. to give a soft capsule formulation having a shell ratio of about 40% and an average capsule size of 650 μm and containing about 1 μg 1α-hydroxyvitamin $D_3$ per 100 mg capsule.

(2) Evaluation of Average Capsule Size, Capsule Size Distribution, Shell Ratio, Shell Thickness, Water Content In Capsule Shell, and Hardness The average capsule size was determined from measurements made on 20 capsules (n=20) using a digital HD microscope VH-7000 (Keyence Corporation).

The capsule size distribution was measured using a ROBOT SHIFTER RPS-85 (Seishin Enterprise Co., Ltd.) according to the sieving method, "Method 2. Analytical Sieving Method" of "Powder Particle Size Determination" in JP13, the second addendum.

To determine the shell ratio, each soft capsule formulation was taken in an amount of about 500 mg and precisely measured for its exact weight. The formulation was ground with a mortar and a pestle, washed three times with hexane to remove the solution encapsulated therein, allowed to stand at room temperature for 2 hours, and then measured for the weight of its capsule shell to calculate the shell ratio as follows.

Shell ratio(%)=(weight of shell/weight of soft capsule formulation)×100

The water content in capsule shell was determined using a part of each shell sample obtained in the shell ratio measurement. Each shell sample was dried under conditions of 105° C. for 2 hours, and the water content was calculated from the shell weight before and after drying as follows.

Water content in capsule shell(%)=[(weight of undried shell−weight of dried shell)/weight of undried shell]×100

The shell thickness was determined using a digital HE microscope VD-7000 from cross-sectional images of the ground capsule shell used in the shell ratio measurement. The maximum, minimum and average thicknesses were measured and averaged over three soft capsules (n=3). Points used for measurement of the maximum, minimum and average thicknesses were appropriately selected and determined by an operator based on monitor images.

The hardness was measured and averaged over 10 soft capsules (n=10) using a particle hardness tester (Okada Seiko Co., Ltd.). The measurement was performed using a 100 g load cell at a speed of 100 μm/second.

As a result, the average capsule size was 620 to 650 μm, regardless of titanium oxide content, and 70% of capsules were distributed between 600 and 710 μm in each case. The shell ratio was 38% to 41%, while the water content was 8% to 9% in each soft capsule formulation. The shell thickness was 46 to 47 μm. The hardness was 300 to 500 g, and there was no significant difference in these parameters among soft capsule formulations.

(3) Evaluation of Light-Stabilization Effect

Each soft capsule formulation prepared using each recipe was taken in an amount of about 2 g and arranged in a single layer in a petri dish, followed by irradiation with white light under accelerated conditions of 600,000 and 1,200,000 lux·h at 25° C. in an accelerated irradiation test apparatus (Light-Tron, model LT-120, Nagano Science Co., Ltd.). 1α-Hydroxyvitamin $D_3$ was quantified by HPLC analysis as follows.

To prepare an internal standard solution (TS solution), n-dodecyl p-hydroxybenzoate (about 2 mg) was precisely metered and dissolved in 2-propanol to give a solution of exactly 200 mL, 10 mL of which was then diluted with 2-propanol to 200 mL. To prepare a standard solution, 1α-hydroxyvitamin $D_3$ (about 2 mg) was precisely metered and dissolved in ethanol to give a solution of exactly 200 mL.

A standard sample for quantification was prepared from placebo capsules manufactured in the same manner except that no medicament was incorporated. Such placebo capsules (about 100 mg) were metered, mixed with water (exactly 2 mL) and the standard solution (exactly 100 μL), and then treated by ultrasonication (5 minutes, 40° C.) to dissolve the capsules. The resulting solution was then supplemented with 2-propanol (4 mL) and the IS solution (2 mL), followed by shaking (5 minutes) and centrifugation (4° C., 3000 rpm, 5 minutes).

To prepare test samples, each soft capsule formulation (about 100 mg) was metered, mixed with water (exactly 2 mL) and ethanol (exactly 100 μL), and then treated by ultrasonication (5 minutes, 40° C.) to dissolve the capsules. The resulting solution was then supplemented with 2-propanol (4 mL) and the IS solution (2 mL), followed by shaking (5 minutes) and centrifugation (4° C., 3000 rpm, 5 minutes).

Liquid fractions (total centrifugation supernatants) collected from the standard sample for quantification and the test samples were evaporated to dryness to remove the medium. The resulting residues were each dissolved in acetonitrile (1 mL), 100 μL of which was then subjected to HPLC analysis (Symmetry C18, 150×4.6 mm I.D., 3.5 μm, Waters; acetonitrile/water/tetrahydrofuran/acetic acid mixture (1350:400:250:1))(detection wavelength: 265 nm; flow rate: 1.0 mL).

Preparation and HPLC quantification of test samples were performed by preparing three samples (n=3) for each recipe of soft capsule formulations. The content was calculated according to the following equation and averaged over three samples.

$$1\alpha\text{-Hydroxyvitamin} D_3 \text{ content } (\mu g/100 \text{ mg } cap.) = \frac{Dt \times ISs \times Ws \times 50}{Ds \times ISt \times Wt}$$

Dt: 1α-Hydroxyvitamin $D_3$ peak area of test sample
Ds: 1α-Hydroxyvitamin $D_3$ peak area of standard sample
ISt: IS peak area of test sample
ISs: IS peak area of standard sample
Wt: Measured weight (mg) of small-sized soft capsule formulation
Ws: Measured weight (mg) of 1α-hydroxyvitamin $D_3$ used during standard sample preparation The remaining percentage was calculated as the ratio of medicament content before and after the accelerated test.

Figure 6:
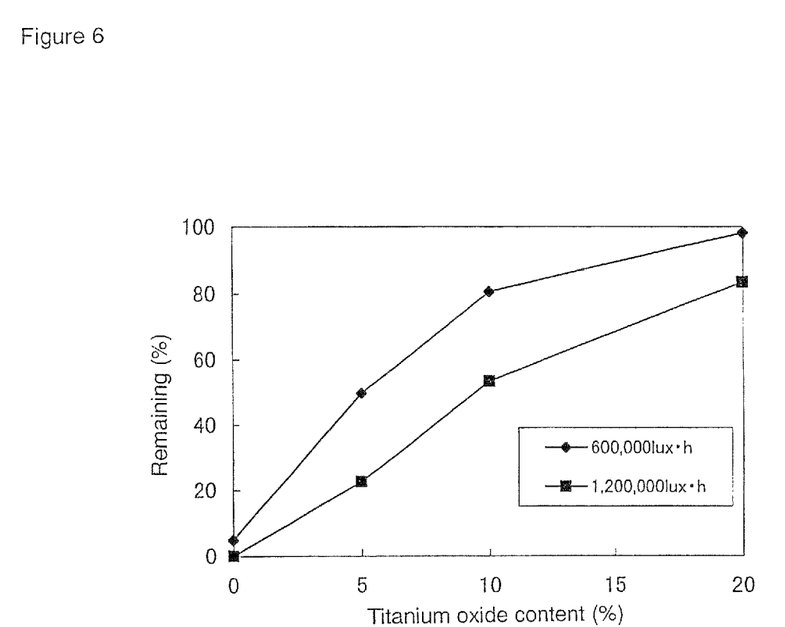
FIG. 6 is a graph showing the results of accelerated irradiation test performed on the soft capsule formulations obtained in Example 3. The vertical axis represents the percentage of remaining 1α-hydroxyvitamin $D_3$ and the horizontal axis represents the titanium oxide content in the shell. The filled diamond and filled square denote the results under accelerated conditions of 600,000 and 1,200,000 lux·h, respectively.

FIG. 6 shows the results obtained. As shown in the figure, the percentage of remaining 1α-hydroxyvitamin $D_3$ increased with increase in titanium oxide content under both conditions. When under 600,000 lux·h, the remaining percentage was 4.9% at 0 wt % titanium oxide, whereas it was 98.1% at 20 wt % titanium oxide. Likewise, when under 1,200,000 lux·h, the remaining percentage was 0% at 0 wt % titanium oxide, whereas it was 83.4% at 20 wt % titanium oxide. These results indicated that the present invention allowed even thin-shelled soft capsule formulations to ensure high light stability.

INDUSTRIAL APPLICABILITY

The light-stabilized soft capsule formulation of the present invention is useful because it ensures effective light shielding of a medicament encapsulated therein.

What is claimed is:

1. A method for manufacturing a soft capsule formulation containing a non-water-soluble light-shielding agent in its shell, comprising:
   (i) the step of preparing a shell-forming solution, comprising the following steps (a) to (c):
       (a) dissolving a gelling agent in medium A;
       (b) dispersing the non-water-soluble light-shielding agent in medium B free from the gelling agent; and
       (c) mixing Medium A containing the gelling agent dissolved therein with Medium B containing the non-water-soluble light-shielding agent dispersed therein; and
   (ii) the step of forming a capsule shell for the soft capsule formulation using the shell-forming solution prepared in the step (i),
   wherein the step of dispersing the non-water-soluble light-shielding agent in Medium B free from the gelling agent is accomplished by ultrasonication.

2. The method for manufacturing a soft capsule formulation according to claim 1, wherein the step of forming a capsule shell for the soft capsule formulation is accomplished by the in-liquid curing coating method.

3. The method of claim 1 wherein Medium B comprises water.

* * * * *